US 8,080,678 B2

(12) United States Patent
Li et al.

(10) Patent No.: US 8,080,678 B2
(45) Date of Patent: Dec. 20, 2011

(54) PURIFICATION OF PROPYLENE OXIDE

(75) Inventors: Xiangmin Li, Glen Mills, PA (US); Lawrence M. Candela, Havertown, PA (US); Brian A Salisbury, Oxford, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 12/798,297

(22) Filed: Apr. 1, 2010

(65) Prior Publication Data
US 2011/0245519 A1    Oct. 6, 2011

(51) Int. Cl.
C07D 301/32    (2006.01)
C07D 301/19    (2006.01)

(52) U.S. Cl. .................... 549/542; 549/541; 549/529

(58) Field of Classification Search .................. 549/529, 549/541, 542
See application file for complete search history.

(56) References Cited

U.S. PATENT DOCUMENTS

| | | | |
|---|---|---|---|
| 2,550,847 A | 5/1951 | Mitchell et al. | |
| 2,622,060 A | 12/1952 | Robeson et al. | |
| 3,350,417 A | 10/1967 | Binning et al. | |
| 3,351,635 A * | 11/1967 | Kollar | 549/529 |
| 3,464,897 A | 9/1969 | Jubin | |
| 3,477,919 A | 11/1969 | Lichtenwalter et al. | |
| 3,578,568 A | 5/1971 | Washall | |
| 3,843,488 A | 10/1974 | Schmidt et al. | |
| 3,881,996 A | 5/1975 | Schmidt | |
| 3,909,366 A | 9/1975 | Schmidt et al. | |
| 4,140,588 A | 2/1979 | Schmidt | |
| 4,691,034 A | 9/1987 | Sanderson et al. | |
| 4,691,035 A | 9/1987 | Sanderson et al. | |
| 4,692,535 A | 9/1987 | Larson et al. | |
| 5,000,825 A | 3/1991 | Shih et al. | |
| 5,006,206 A | 4/1991 | Shih et al. | |
| 5,106,458 A | 4/1992 | Meyer et al. | |
| 5,107,002 A | 4/1992 | Shih | |

\* cited by examiner

*Primary Examiner* — Taylor Victor Oh

(57) ABSTRACT

The invention is a method of purifying propylene oxide containing 25-100 ppm aldehyde impurities. The method comprises contacting the propylene oxide in the liquid phase with an amine-functionalized ion exchange resin, and recovering a purified propylene oxide product containing 10 ppm, or less, aldehydes.

11 Claims, No Drawings

PURIFICATION OF PROPYLENE OXIDE

FIELD OF THE INVENTION

This invention relates to the purification of propylene oxide.

BACKGROUND OF THE INVENTION

Propylene oxide (PO) is a valuable chemical that is used to make propylene glycol, propylene glycol ethers, 1,4-butanediol, and polyols for use in the production of polyurethane materials. Generally, PO is formed by reacting propylene with an oxidizing agent in the presence of a catalyst. PO is commercially produced by reacting propylene with an organic hydroperoxide, such as ethyl benzene hydroperoxide, cumene hydroperoxide or tert-butyl hydroperoxide, in the presence of a solubilized molybdenum catalyst or a heterogeneous titania-on-silica catalyst. PO is also produced by the reaction of propylene and hydrogen peroxide in the presence of a titanium silicate catalyst.

In these processes, small amounts of hydrocarbons and oxygen-containing byproducts, such as methanol, acetone, methyl formate, and aldehydes, are produced. Many methods have been developed to remove these impurities from PO. Previous disclosed methods include extractive distillation techniques which utilize: $C_8$ to $C_{20}$ alkanes, alkenes or naphthenes, $C_6$ to $C_{12}$ aromatic hydrocarbons, $C_8$ to $C_{12}$ aliphatic or cyclic paraffins, and a tertiary butyl alcohol-water mixture to remove contaminating hydrocarbons (see U.S. Pat. Nos. 3,843,488, 3,909,366, 3,464,897, 5,006,206); and water or lower glycols such as ethylene glycol and propylene glycol to remove oxygen-containing impurities (see U.S. Pat. Nos. 4,140,588, 3,578,568 and 5,000,825).

Other purification processes include methods to remove methyl formate by contacting crude PO with alkali metal hydroxides, including: an aqueous alkali metal hydroxide solution (see U.S. Pat. No. 2,622,060); an aqueous solution of an alkaline saponifying agent (see U.S. Pat. No. 2,550,847); an aqueous slurry of calcium hydroxide (see U.S. Pat. No. 3,477,919); and sodium hydroxide in water and glycerol (see U.S. Pat. No. 4,691,035). Other methods include using a combination of distillation and a caustic treatment to simultaneously aldolize acetaldehyde and saponify methyl formate (see U.S. Pat. No. 3,350,417) and treating with an aqueous calcium hydroxide slurry to which a solubilizer and an aldehyde scavenger are added (see U.S. Pat. No. 4,691,034).

Adsorption techniques have also been taught to remove high levels of impurities, including the removal of high molecular weight ethers from PO by treatment with an absorbent such as activated carbon (see U.S. Pat. No. 4,692,535) and the removal of methyl formate from contaminated PO by contacting with a basic ion exchange resin (see U.S. Pat. Nos. 5,107,002 and 5,106,458).

Commercially useful techniques include plural stage distillation processes to purify PO. See, for example, U.S. Pat. No. 3,881,996. This patent discloses distilling crude, propylene-free PO to remove acetaldehyde as an overhead product, then distilling the bottoms stream to separate PO as an overhead product from propionaldehyde and other higher boiling materials. This method can produce PO having very low levels of aldehyde (less than 10 ppm). However, distillation processes are extremely energy-intensive and there is a significant energy input required to achieve such low levels of aldehyde.

For most applications, it is important to reduce the amount of aldehyde impurities to about 30-50 ppm, or lower. However, for a minor number of applications, it is necessary to reduce the aldehyde impurity level to 10 ppm or lower.

In sum, new methods for the purification of propylene oxide are needed. We have discovered an effective, convenient method to purify propylene oxide.

SUMMARY OF THE INVENTION

The invention is a method of purifying propylene oxide which contains 25-100 ppm aldehyde impurities. The method comprises contacting the propylene oxide in the liquid phase with an amine-functionalized ion exchange resin, and recovering a purified propylene oxide product having 10 ppm, or less, aldehydes content.

DETAILED DESCRIPTION OF THE INVENTION

Propylene oxide is a well-known chemical compound that is available from Lyondell Chemical Company and other producers. The propylene oxide having an aldehyde content of 25-100 ppm, and preferably 25-50 ppm, may be produced by any known process, but is preferably the product of the reaction of propylene with an organic hydroperoxide such as ethyl benzene hydroperoxide, cumene hydroperoxide or t-butyl hydroperoxide. The epoxidation process is described in U.S. Pat. Nos. 3,351,635 and 4,367,342. This epoxidation reaction preferably occurs in the presence of a solubilized molybdenum catalyst or a heterogeneous titania on silica catalyst. The epoxidation reaction effluent is subjected to one or more distillation steps in order to produce a propylene oxide product stream.

Propylene oxide, as formed by the reaction of propylene with an organic hydroperoxide, contains various impurities. These impurities include aldehydes, acetone, methanol, methyl formate, hexenes, and water. The aldehyde impurities comprise acetaldehyde and propionaldehyde. For example, a crude propylene oxide product produced by the reaction of propylene and an organic hydroperoxide such as ethyl benzene hydroperoxide, from which unreacted propylene has been removed by prior distillation according to conventional fractional distillation operations, typically contains 92-99 wt. % propylene oxide, 0.05-2 wt. % (500-20,000 ppm) acetaldehyde, and 0.05-2 wt. % propionaldehyde, plus other impurities.

Following the reaction of propylene with an organic hydroperoxide such as ethyl benzene hydroperoxide, the propylene oxide product mixture is generally first distilled to separate unreacted propylene overhead from heavier components. The separated propylene is conveniently recycled to the epoxidation step. The heavier components are then further distilled after a caustic wash step in a series of distillations to separate propylene oxide product, product 1-phenyl ethanol, and unreacted ethyl benzene which can be recycled, preferably after a caustic wash as described in U.S. Pat. No. 3,439,001. The 1-phenyl ethanol stream is dehydrated to product styrene monomer in accordance with known procedures such as described in U.S. Pat. No. 3,351,635.

Distillation can produce purified propylene oxide containing very low levels of aldehyde impurities. However, in order to produce propylene oxide having an aldehydes content of 10 ppm or less, the distillation has very high energy requirements that result in significant production cost. Because few applications require an aldehyde content of 10 ppm or less, significant production savings could result in a process in which propylene oxide is first distilled to an aldehydes content of 25-100 ppm and then aldehydes are lowered to 10 ppm or less through a less costly process.

Thus, preferably the method of the invention comprises first reacting propylene and an organic hydroperoxide to produce a crude propylene oxide effluent, and then distilling the crude propylene oxide effluent to produce a propylene oxide stream containing 25-100 ppm aldehydes, more preferably 25-50 ppm. The propylene oxide stream containing 25-100 ppm aldehydes is then contacted in the liquid phase with an amine-functionalized ion exchange resin, and recovered to produce a purified propylene oxide product having 10 ppm, or less, aldehydes content.

In order to reduce the level of aldehyde impurities in the propylene oxide from 25-100 ppm down to 10 ppm or less, the propylene oxide is contacted in the liquid phase with an amine-functionalized ion exchange resin. In accordance with the present invention, the impure propylene oxide is contacted in the liquid phase with an amine-functionalized ion exchange resin adsorbent whereby aldehyde impurities are retained on the amine-functionalized ion exchange resin and a purified propylene oxide product reduced in aldehyde impurities content is conveniently separated.

The amine-functionalized ion exchange resin adsorbent useful in the invention is a solid material that consists of a macroporous polystyrene divinylbenzene cross-linked copolymer which has been functionalized with amine groups and supplied as the free base. Preferably, the amine-functionalized ion exchange resin is a benzyl amine-functionalized ion exchange resin, wherein the cross-linked copolymer has been functionalized with benzyl amine groups. Specific commercially available amine-functionalized ion exchange resins include Lewatit® VP OC 1065 (a product of Lanxess).

In general, suitable amine-functionalized ion exchange resin adsorbents are further characterized by having a relatively large surface area in relation to their mass. The amine-functionalized ion exchange resin adsorbents for purpose of this invention preferably have a surface area of at least 200 m²/g, and more preferably the average surface area is from 400 m²/g to 1500 m²/g.

Adsorption is preferably carried out by passing the impure propylene oxide through a bed of amine-functionalized ion exchange resin adsorbent. The invention may be carried out in a continuous or batch-wise fashion in accordance with known procedures. Continuous operation is preferred, as is the use of a plurality of adsorbent contact zones. When a plurality of adsorbent contact zones are used, one zone may be in use while adsorbent in a second zone is regenerated. The use of three contact zones is particularly preferred, with two zones in use at the same time, one a lead contact zone and the second a polishing zone, while the third zone is regenerated.

The adsorptive contact is conveniently carried out at moderate temperatures. Suitable temperatures are in the range of about 10° C. to 100° C., preferably 15° C. to 60° C. In general, higher adsorption temperature reduces adsorption capacity. Therefore, to maximize adsorption capacity of the amine-functionalized ion exchange resin adsorbent, it is preferable to control the adsorption temperature within the range of about 20° C. to 40° C. Flow rates of about 0.005 to 50 volumes of propylene oxide per volume of adsorbent per hour are preferred, more preferably about 0.02-5. In general, slower feed flow rate reduces product impurity at a given bed-volume. Therefore, flow rate may be optimized depending on the volume of adsorbent utilized in the method.

The amine-functionalized ion exchange resin adsorbent retains the impurities adsorbed thereon and purified propylene oxide can be separated. Initially, there can be substantially complete removal of the aldehyde impurities and the recovered propylene oxide is of exceptional purity. Over the course of time the amine-functionalized ion exchange resin gradually become less effective for the removal of these impurities.

Thus, when the separation efficiency of the amine-functionalized ion exchange resin adsorbent has fallen below a desired point, the adsorbent is preferably regenerated. The adsorbent is preferably regenerated by one or multiple cycles of light caustic washes and/or water washes. It is advantageous to employ a plurality of parallel contact zones such that while one zone is being regenerated the feed is passed through a zone containing fresh or regenerated contact material so that optimum impurities removal can be achieved.

Following the purification method, a purified propylene oxide product having decreased aldehyde impurities content of 10 ppm, or less, is recovered.

The following examples merely illustrate the invention. Those skilled in the art will recognize many variations that are within the spirit of the invention and scope of the claims.

Example 1

Adsorption Runs

A stainless steel tube (1 inch I.D.×2 ft.) is packed with various adsorbents (Ex. 1A: Lewatit® VP OC 1065, a benzyl amine-functionalized ion exchange resin; Comp. Ex. 1B-1E: molecular sieve 13X, alumina, carbon, silica). The tube is placed in an electric furnace and the temperature is controlled to 28° C. The feed of propylene oxide (containing 21-38 ppm acetaldehyde) is passed upflow through the bed at a LHSV from 0.1-0.15 h⁻¹. Samples are collected while up to 21 bed volumes (BV) are passed through the bed. The samples are analyzed by liquid chromatography (LC) for acetaldehyde content. Results are shown in Table 1.

The results show that the amine-functionalized ion exchange resin effectively removes low levels of acetaldehyde from the propylene oxide feed.

Example 2

Continuous Plug-Flow Run

A stainless steel tube (1 inch I.D.×2 ft.) is packed with Lewatit® VP OC 1065. The tube is placed in an electric furnace and the temperature is controlled to 28° C. The feed of propylene oxide (containing 17-30 ppm acetaldehyde and 11-70 ppm propionaldehyde; amounts shown in Table 2) is passed upflow through the bed at a LHSV from 1 h⁻¹ and samples are collected periodically. The propylene oxide feed is passed through the bed for a total of 256 bed volumes (BV). The samples are analyzed by LC for acetaldehyde and propionaldehyde content. Breakthrough occurs after 210 BV. For the first 210 BV tested, acetaldehyde is reduced to ~1-3 ppm. Propionaldehyde is also reduced. Results are shown in Table 2.

TABLE 1

Adsorption Run Data for Various Adsorbents

| | | | Acetaldehyde | |
|---|---|---|---|---|
| Run # | Adsorbent | # BV | Feed | Product |
| 1A | Lewatit VP OC 1065 | 21 | 26-38 | <1 |
| 1B* | Molecular Sieve 13X | — | ineffective | |

TABLE 1-continued

Adsorption Run Data for Various Adsorbents

| Run # | Adsorbent | # BV | Acetaldehyde Feed | Acetaldehyde Product |
|---|---|---|---|---|
| 1C* | Activated Alumina | 5 | 21 | 18 |
| 1D* | Activated Carbon | 3.7 | 26 | 18 |
| 1E* | Silica Gel | 7.4 | 38 | 25 |

*Comparative Example

TABLE 2

Continuous Adsorption Run Data

| # BV | Acetaldehyde, ppm Feed | Acetaldehyde, ppm Product | Propionaldehyde, ppm Feed | Propionaldehyde, ppm Product |
|---|---|---|---|---|
| 0.6-24 | 25 | 3 | 69 | 8 |
| 24-159 | 17 | 1 | 26 | 7 |
| 159-210 | 30 | 1 | 12 | 6 |
| 210-256 | 30 | 9 | 12 | 11 |

We claim:

1. A method of purifying propylene oxide containing 25-100 ppm aldehydes which comprises contacting the propylene oxide in the liquid phase with a benzyl amine-functionalized ion exchange resin, and recovering a purified propylene oxide product having 10 ppm, or less, aldehydes content.

2. The method of claim 1 wherein the aldehydes comprise acetaldehyde and propionaldehyde.

3. The method of claim 1 wherein the amine-functionalized ion exchange resin has a surface area in the range of 400 to 1500 $m^2/g$.

4. The method of claim 1 wherein the propylene oxide is produced by the reaction of propylene and an organic hydroperoxide.

5. The method of claim 4 wherein the organic hydroperoxide is ethyl benzene hydroperoxide, t-butyl hydroperoxide, or cumene hydroperoxide.

6. The method of claim 1 wherein the propylene oxide contains 25-50 ppm aldehydes.

7. A method which comprises reacting propylene and an organic hydroperoxide to produce a crude propylene oxide effluent, distilling the crude propylene oxide effluent to produce a propylene oxide stream containing 25-100 ppm aldehydes, contacting the propylene stream in the liquid phase with a benzyl amine-functionalized ion exchange resin, and recovering a purified propylene oxide product having 10 ppm, or less, aldehydes content.

8. The method of claim 7 wherein the organic hydroperoxide is ethyl benzene hydroperoxide, t-butyl hydroperoxide, or cumene hydroperoxide.

9. The method of claim 7 wherein the aldehydes comprise acetaldehyde and propionaldehyde.

10. The method of claim 7 wherein the amine-functionalized ion exchange resin has a surface area in the range of 400 to 1500 $m^2/g$.

11. The method of claim 7 wherein the propylene oxide stream contains 25-50 ppm aldehydes.

* * * * *